(12) United States Patent
Jones et al.

(10) Patent No.: US 12,098,360 B2
(45) Date of Patent: Sep. 24, 2024

(54) PROBE

(71) Applicant: ABER INSTRUMENTS LIMITED, Aberystwyth Dyfed (GB)

(72) Inventors: Steffan Jones, Aberystwyth Dyfed (GB); Peter Twiddy, Aberystwyth Dyfed (GB); Tim Pryce, Aberystwyth Dyfed (GB)

(73) Assignee: ABER INSTRUMENTS LIMITED, Aberystwyth Dyfed (GB)

( * ) Notice: Subject to any disclaimer, the term of this patent is extended or adjusted under 35 U.S.C. 154(b) by 0 days.

(21) Appl. No.: 16/772,618

(22) PCT Filed: Dec. 13, 2018

(86) PCT No.: PCT/GB2018/053624
§ 371 (c)(1),
(2) Date: Jun. 12, 2020

(87) PCT Pub. No.: WO2019/116043
PCT Pub. Date: Jun. 20, 2019

(65) Prior Publication Data
US 2021/0071130 A1    Mar. 11, 2021

(30) Foreign Application Priority Data
Dec. 13, 2017    (GB) .................................... 1720761

(51) Int. Cl.
*C12M 1/00*  (2006.01)
*C12M 1/12*  (2006.01)
(Continued)

(52) U.S. Cl.
CPC ............ *C12M 41/36* (2013.01); *C12M 23/28* (2013.01); *C12M 37/04* (2013.01); *C12M 41/48* (2013.01)

(58) Field of Classification Search
CPC ...... C12M 41/36; C12M 23/28; C12M 37/04; C12M 41/48; C12M 41/00; C12M 1/3407; G01N 33/48735
(Continued)

(56) References Cited

U.S. PATENT DOCUMENTS

| 4,309,506 A | 1/1982 | Squires |
| 4,893,935 A | 1/1990 | Mandel et al. |

(Continued)

FOREIGN PATENT DOCUMENTS

| EP | 2 065 701 A2 | 6/2009 | |
| WO | 2010017519 A1 | 2/2010 | |
| WO | WO-2015152219 A1 * | 10/2015 | ........... G01N 27/283 |

OTHER PUBLICATIONS

PCT International Search Report and Written Opinion for corresponding PCT/GB2018/053624, mailed Mar. 12, 2019.

(Continued)

*Primary Examiner* — Liban M Hassan
(74) *Attorney, Agent, or Firm* — Troutman Pepper Hamilton Sanders LLP (Rochester)

(57) ABSTRACT

This invention relates to a system for obtaining a biomass measurement from a medium contained within a bioreactor. The system comprises a bioreactor having a port comprising an annular flange (15) and an upstanding collar (19), and a biomass sensing probe comprising an elongate body and at least one electrode (3) provided on a first region (1) of the body. The port is configured to receive the probe and form a watertight seal with the probe when it is located in the port with the first region (1) of the body exposed to the interior of the bioreactor.

20 Claims, 2 Drawing Sheets

(51) Int. Cl.
*C12M 1/34* (2006.01)
*C12M 1/36* (2006.01)

(58) Field of Classification Search
USPC .......................................... 435/288.7, 289.1
See application file for complete search history.

(56) References Cited

U.S. PATENT DOCUMENTS

| | | | |
|---|---|---|---|
| 5,174,325 A | | 12/1992 | Okel et al. |
| 8,988,082 B2 * | | 3/2015 | Selman .................. C12M 41/36 |
| | | | 324/649 |
| 2004/0122280 A1 * | | 6/2004 | Forney ...................... G01J 3/02 |
| | | | 600/2 |
| 2005/0239198 A1 | | 10/2005 | Kunas et al. |
| 2008/0319583 A1 * | | 12/2008 | Hagerty .................. C08F 10/00 |
| | | | 700/269 |
| 2009/0050476 A1 * | | 2/2009 | Zhang .................... G01N 27/30 |
| | | | 204/290.12 |
| 2009/0151482 A1 * | | 6/2009 | Klees ...................... G01D 21/00 |
| | | | 73/866.5 |
| 2011/0097789 A1 | | 4/2011 | Goodwin et al. |
| 2011/0107857 A1 | | 5/2011 | Pfauch et al. |
| 2011/0124035 A1 * | | 5/2011 | Broadley ............... C12M 23/28 |
| | | | 435/29 |
| 2011/0260738 A1 | | 10/2011 | Selman et al. |
| 2014/0260712 A1 * | | 9/2014 | Damren ................. G01D 11/24 |
| | | | 73/866.5 |
| 2015/0185173 A1 | | 7/2015 | Potyrailo et al. |
| 2016/0174545 A1 * | | 6/2016 | Parra .................... A01N 1/0257 |
| | | | 435/284.1 |

OTHER PUBLICATIONS

UK Search Report for corresponding GB 1720761.4, mailed Jul. 31, 2018.

Gavin B. Matthew, "The Use of Capacitance Measurement in Fermentation Monitoring," Department of Chemical and Biochemical engineering, University College London Sep. 1999.

* cited by examiner

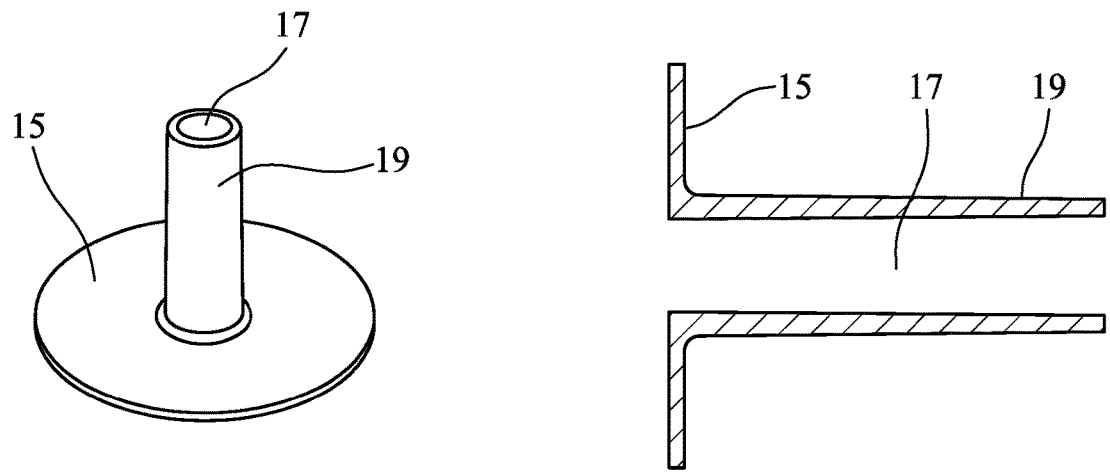
Figure 4
Figure 5
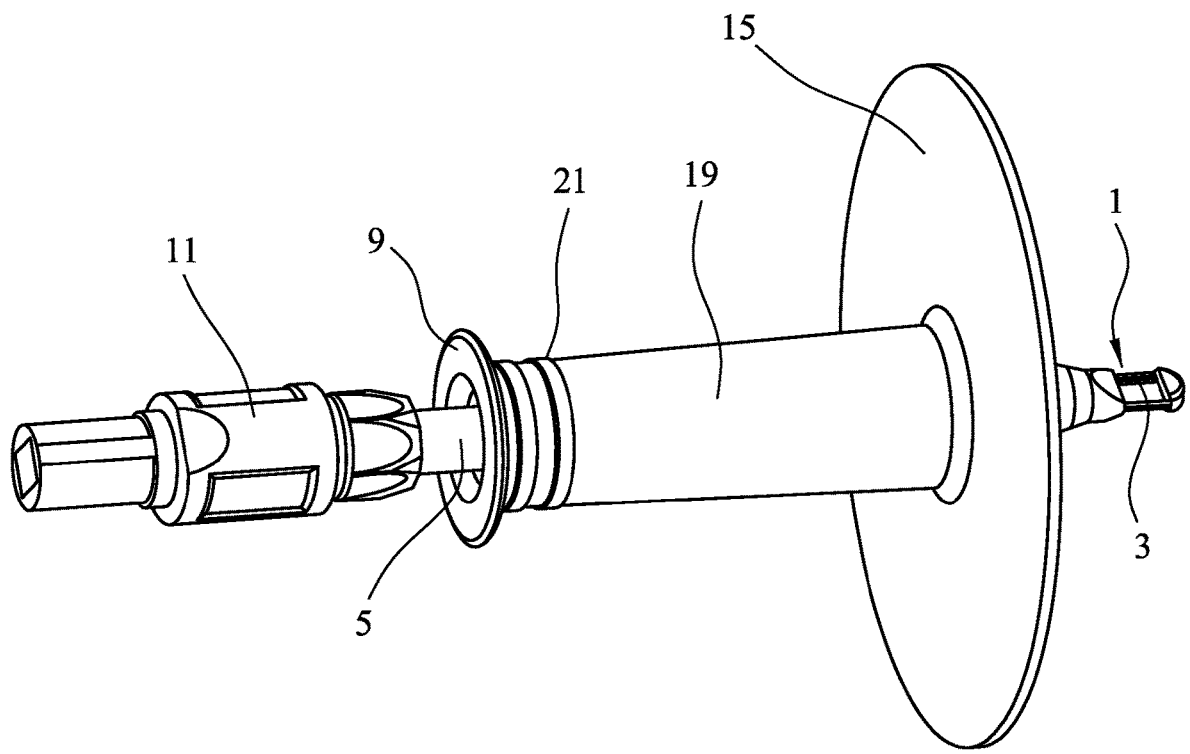
Figure 6

PROBE

This application is a national stage application under 35 U.S.C. § 371 of PCT Application No. PCT/GB2018/053624, filed Dec. 13, 2018, which claims the priority benefit of Great Britain Patent Application No. 1720761.4, filed Dec. 13, 2017.

BACKGROUND OF THE INVENTION

Capacitance measurement techniques are known for measuring the capacitance (or specific capacitance or dielectric constant) of liquids and suspensions, such as biological cells in ionic aqueous solutions.

Monitoring systems incorporating such measurement capability are beneficial for measuring concentration of live cells. In particular in the brewing industry, the concentration of live yeast can be measured with an on-line capacitance probe. A radio frequency applied from the electrodes of the probe causes ions in the suspending medium (for example wort or green beer) and the cytoplasm of the yeast to move towards the two respective oppositely charged electrodes.

As the plasma membrane is non-conducting a build up of charge results in the cells and are said to be polarised with the yeast cells acting as tiny capacitors within the medium. Non-viable cells or cells with a damaged membrane do not interfere with the signal. Thus, a build up of charge cannot occur as the ions can freely move across the membrane and so the cells do not become polarised.

The measured capacitance is directly proportional to the amount of viable yeast within a sample over a wide concentration range.

In addition to the brewing industry, such technology can also be utilised for measuring biomass in the field of biotechnology, for example, in controlling cell culture processes.

In certain applications, whether brewing, biotechnological or other fields of industry, it is desirable to use 'single use' processing equipment. In such applications, single use bioreactors may be employed. As their name suggests, such bioreactors are configured to be used for only a single fermentation process, before being disposed of.

A range of single use bioreactors are commercially available and will be known to those skilled in the art. Examples of such bioreactors have been commercialised under the trade names HyPerforma by Thermo-Fisher, or FlexSafe® by Sartorius.

In addition to the bioreactors employed in such applications being 'single use', it may also be desirable for the components used to monitor properties of the biomass medium housed within the bioreactor to also be intended for 'single use'.

Conventionally, attempts have been made to provide single use bioreactors with measurement components integrally formed within the walls of the bioreactors and in this connection, reference may be made to the arrangements disclosed in EP2307879. Those arrangements include configurations in which a disc-shaped body having an annular flange is positioned within an opening in the bioreactor wall, with the annular flange being adhered or welded to the bioreactor wall.

While arrangements of this type do provide a straightforward configuration permitting the monitoring of properties of the biomass medium within the bioreactor, there are a number of drawbacks associated with their use. Firstly, the electrodes do not project significantly into the bioreactor, meaning that, in order for reliable measurements to be taken, the bioreactor must be oriented such that the electrodes are in constant contact with the medium within the bioreactor. This can be problematic depending on the volume of the biomass within the reactor and/or the arrangement of the location in which the bioreactor is located.

Secondly, as the electrodes are integrally formed with the bioreactor, in the event that any defect with the electrodes is detected prior to use of the bioreactor, the entire bioreactor will have to be disposed of.

Accordingly, there is a need for apparatus which can be used to measure properties of a biomass medium in a single use bioreactor which overcomes one or more of these shortcomings of the prior art.

Thus, according to a first aspect of the invention, there is provided a system for obtaining a biomass measurement from a medium contained within a bioreactor, the system comprising a bioreactor having a wall enclosing an interior, the wall comprising a port; a biomass sensing probe comprising an elongate body having a distal end and at least one electrode provided on a first region of the body at the distal end of the probe; the port being configured to receive the probe and form a watertight seal with the probe when the probe is located in an operative position within the port, wherein in the operative position the first portion of the body is exposed to the interior of the bioreactor.

BRIEF DESCRIPTION OF THE DRAWINGS

FIG. 4 is a perspective view of a port with which the probe shown in FIG. 3 can be used to form a watertight seal.

FIG. 5 is a sectional view of the port shown in FIG. 4.

FIG. 6 shows the probe of FIG. 3 installed in an operative position in the port of FIG. 4.

DETAILED DESCRIPTION

Figure 1:
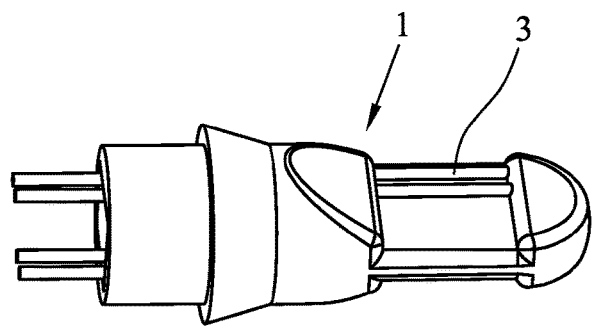
FIG. 1 is a perspective view of a probe tip bearing four electrodes (two are visible).

To the inventors' knowledge, no single use bioreactor configured for use with a single use elongate probe for measuring capacitance has been commercialised previously. Through the provision of a biomass sensing probe and bioreactor as separate components, this permits the user of the bioreactor to select a specific probe if there are a choice of these available to him or her. Additionally, in the event that the user, upon carrying out pre-use validation of the apparatus, identifies that the biomass sensing probe he or she is planning on using is defective, this can be discarded and a functioning probe used, which would not be possible in arrangements where the probe (or other component) bearing electrodes is integrally formed with the bioreactor (such as disclosed in EP2307879).

As explained above, the port of the bioreactor is configured to receive the probe and form a watertight seal with the probe when the probe is located in an operative position within the port. For the avoidance of doubt, as used herein, the term 'watertight' means that, when the probe is located in the operative position within the port, substantially no moisture (or more preferably no moisture at all) is capable of passing through the port. The skilled person will be familiar with methods for testing seals.

In one embodiment, the seal strength of the probe and port may be determined by i) placing the probe in an operative position within the port, filling the bioreactor with room temperature water, exerting a pressure of 1 bar within the bioreactor and determining the egress of moisture from the bioreactor via the port. The seal strength formed between the port and the probe when located in the operative position preferably permits moisture egress of about 0.1 ml/24 h or less, about 0.05 ml/24 h or less, about 0.02 ml/24 h or less, about 0.01 ml/24 h or less, about 0.005 ml/24 h or less, about 0.002 ml/24 h or less or about 0.001 ml/24 h or less. In certain embodiments of the invention, no moisture egress via the port is detected in a 24 hour testing period.

The watertight seal may be attained through the profile of the biomass sensing probe and the interior of the port forming a watertight seal therebetween. Any configuration of the probe/port profiles may be selected provided that this provides a watertight seal.

For the avoidance of doubt, the port is not simply an opening in the wall of the bioreactor, but a component or formation configured to facilitate the achievement of a watertight seal with the biomass sensing probe while providing access to the interior of the bioreactor. It may be a separate component to the bioreactor which may be fixed thereto, for example by adhesion, welding or the like. Alternatively, the bioreactor may be produced such that the port is an integral part of the bioreactor wall.

The port can have any shape and profile provided that it permits the formation of a watertight seal with the biomass sensing probe while providing access to the interior of the bioreactor. In one embodiment, the port may comprise a channel having a longitudinal axis, through which the biomass sensing probe may be inserted. The port may comprise a collar which defines the channel.

The channel can have any shape and profile provided that it permits the formation of a watertight seal with the biomass sensing probe while providing access to the interior of the bioreactor.

The channel/port may have an inner end (which is closest to the interior of the bioreactor and through which the first portion of the body of the biomass sensing probe will be exposed to the interior of the bioreactor when the probe is in the operative position) and an outer end (which is furthest from the interior of the bioreactor and through which the first portion of the body of the biomass sensing probe will be inserted prior to being located in the operative position).

The channel may be of substantially constant cross-sectional area and/or diameter, may be tapered (e.g. such that the diameter of the channel at its outer end is greater than at its inner end or vice versa), stepped, and/or arranged in any other way to facilitate the formation of a watertight seal with the biomass sensing probe.

The channel may have any shape in cross section, e.g. circular, square, diamond-shaped, rectangular, hexagonal, or another polygonal shape.

The channel may have a diameter ranging from about 3 mm, about 5 mm or about 7 mm to about 10 mm, about 12 mm, about 15 mm, about 19 mm or about 25 mm. The length of the channel from its inner end to its outer end may range from about 10 mm, about 20 mm, about 50 mm, about 70 mm, about 100 mm, to about 150 mm, about 200 mm, about 250 mm, about 300 mm, about 350 mm, about 400 mm, about 450 mm, about 500 mm, about 600 mm or about 700 mm. Alternatively, the length of the channel may be greater than about 700 mm.

In embodiments of the invention, the longitudinal axis of the channel may be substantially perpendicular to the plane of the wall of the bioreactor. The inner end of the port/channel may be positioned in the interior of the bioreactor, in the plane of the wall of the bioreactor or externally of the wall of the bioreactor.

The at least one electrode may extend along a portion of the outer surface of the body and/or may be positioned only at the distal end of the body. The electrode/s may extend longitudinally along a part of or all of the body. Additionally or alternatively, the electrode/s may have an annular configuration, extending around a part of the body, or be trapezoidally arranged on the probe, e.g. at its end. Examples of how electrodes may be configured in elongate probes are disclosed in UK Patent No. 2507283, the contents of which are incorporated herein by reference.

The at least one electrode may be connected to one or more conducting means (e.g. wires, tracks or the like) to carry the biomass reading signal to a position distant from the electrode/s. Such conducting means may be positioned within the body of the probe.

The bioreactor may take any form. It may be a reusable bioreactor, for example a fermenter formed from stainless steel, glass, plastic and may have a capacity ranging from sub-litre (e.g. 10 mL to about 950 mL) to industrial scale, e.g. about 10,000 L, about 50,000 L or about 100,000 L. Alternatively, the bioreactor may be a single use bioreactor, for example a bag type bioreactor (e.g. marketed by Applikon, Broadley James, Cellexus, Eppendorf, Finesse, GE Lifesciences, Infors, Pall, or Sartorius Stedim) or a vessel type bioreactor (e.g. one marketed under the brand name HyPerforma by Thermo-Fisher).

In one arrangement of the invention, the biomass sensing probe body may have a tapered profile, for example such that the diameter and/or cross-sectional area of the biomass sensing probe body is smaller at the distal end of the probe than at a position remote from the distal end of the probe. In such an arrangement, the probe body can be considered to have an outwardly tapering profile when viewed along the body from its distal end.

The biomass sensing probe body may have any shape in cross section, e.g. circular, square, diamond-shaped, rectangular, hexagonal, or another polygonal shape. In embodiments of the invention, the profile of the biomass sensing probe body is shaped to conform to the profile of the channel in the port.

The body of the biomass sensing probe may have a diameter ranging from about 3 mm, about 5 mm or about 7 mm to about 10 mm, about 12 mm, about 15 mm, about 19 mm or about 25 mm. The length of the body may range from about 50 mm, about 70 mm, about 100 mm, about 150 mm, or about 200 mm to about 250 mm, about 300 mm, about 350 mm, about 400 mm, about 450 mm, about 500 mm, about 600 mm or about 700 mm. Alternatively, the length of the body may be greater than about 700 mm.

The body of the biomass sensing probe may be monolithic (i.e. formed from a single component) or may be modular (i.e. formed from a plurality of probe body components). For example, in a modular arrangement, the body of the biomass sensing probe may comprise a core (e.g. which provides the probe with sufficient rigidity to enable it to be fed through the port into its operative position) and a shell (e.g. which provides the probe with an external profile to facilitate the formation of a watertight seal with the port). In such embodiments, the shell may be monolithic or may be modular. Additionally or alternatively, the shell may surround the entirety of the core or may partially surround the core, e.g. such that a portion of the core (which may be the portion of the probe which is exposed to the interior of the bioreactor when the probe is in the operative position, and/or the first region of the probe) is exposed.

In modular arrangements, the probe body may comprise a tip (e.g. which comprises the at least one electrode) at its distal end as probe body component which is optionally solid.

The body of the biomass sensing probe may be hollow to permit conducting means (e.g. wires, tracks or the like) to pass through its interior which conducting means are connected to the electrode/s. Alternatively, the probe body may be solid and optionally have conducting means moulded into its interior, which conducting means can be connected to the at least one electrode.

The biomass sensing probe may contain any number of electrodes. For example, the probe may contain 1, 2, 3, 4, 5, 6, 7, 8 or more than 8 electrodes. In embodiments of the invention, the probe may contain 2 to 6 or 2 to 4 electrodes.

Those skilled in the art will be familiar with materials from which the at least one electrode may be formed or plated. As examples, the electrode/s may be formed of or plated with gold, stainless steel, iridium, platinum (e.g. platinum black) and any other material with low or controllable electrode polarisation properties.

The biomass sensing probe may comprise conducting means (e.g. tracks which may be formed in printed circuit board (PCB) or in the body of the probe, wires, or the like) to carry biomass signals to a location remote from the at least one electrode. The conducting means may be formed from any electrically conductive material, for example copper.

In embodiments of the invention, the probe may be equipped with data storage means, for example a microchip. The data storage means may store information such as calibration correction values, serial and/or part numbers, temperature values or other information.

In embodiments of the invention, the system further comprises biomass signal processing means. Such means are used to take a biomass reading. Those skilled in the art will be familiar with biomass signal processing means, for example the Futura® range of systems (Aber Instruments Limited).

The biomass signal processing means are preferably in communication with the probe to enable the transmission of biomass signals from the probe to the biomass signal processing means. For example, the connection between the biomass sensing probe and the biomass signal processing means may be a cable. The cable may be removably coupled to the probe.

In a further embodiment, the connection between the probe and the biomass signal processing means may be wireless, e.g. via WLAN, bluetooth, RFID, NFC, or the like.

In embodiments in which the biomass sensing probe is removably coupled to other components, e.g. to a cable or directly to the biomass signal processing means, the probe may be provided with coupling means to enable the probe to be connected to other components. In embodiments of the invention, the coupling means comprises a plug/socket part (e.g. which is complementary to the component to which the probe is to be connected), a slide connector, a push-pull connector (e.g. as commercialised by Redel), a flexible catch, a magnetic connector and/or a screwed connector.

In embodiments the probe may be provided pre-sterilised, i.e. so that it can be used without the need for a prior sterilisation step. In such embodiments, the probe may be provided in sterile packaging.

The term 'operative position' as used herein means a position in which the biomass sensing probe is positioned within the port such that both i) a watertight seal is established between the probe and the port, and ii) the at least one electrode is located within the interior of the bioreactor such that a biomass measurement can be obtained from a medium contained therein. To facilitate the placement of the biomass sensing probe within an operative position within the port, the port and/or the biomass sensing probe may be provided with positioning means, i.e. feature/s which facilitate the location of the probe in an operative position.

For example, such positioning means could comprise over-insertion prevention means which could take the form of a formation provided on the port and/or the probe to prevent over-insertion of the probe into/through the port. Such a formation could, for example, take the form of an annular flange and/or series of projections provided on the probe and/or port.

The probe and/or port may be provided with probe retention means which function to retain the probe in the operative position once located in that position. The probe retention means may comprise a locking mechanism (e.g. a snap-fit connection) provided on the probe and/or the port, threading provided on the probe and/or port to permit those components to be screwed together and/or bands which compress the port to reduce its diameter.

The body of the probe, the portion of the probe which is exposed to the interior of the bioreactor when the probe is in the operative position, and/or the first region of the probe may be formed of any material which will meet the functional requirements of the probe during use. For example, the body of the probe, the portion of the probe which is exposed to the interior of the bioreactor when the probe is in the operative position, and/or the first region of the probe may be formed of metal or plastics material. For single use applications, owing to reduced cost and complexity of manufacture, plastics may be preferable.

Examples of plastics materials that may be used to form the body of the probe, the portion of the probe which is exposed to the interior of the bioreactor when the probe is in the operative position, and/or the first region of the probe include from liquid crystal polymer, phenolic polymer, nylon, polyethylene, polypropylene, polystyrene, polyvinylidene fluoride, polyvinylchloride, acrylonitrile butadiene styrene, acetal resins, sulphone, polysulphone, polyamide, polyphenylene sulphide, polyetheretherketone, polyethylene terephthalate, polyetherketone, polyoxymethylene, polyphthalamide, polyetherketoneketone, thermoplastic polyimide, polyacrylate, polytetrafluoroethylene, polymethyl methacrylate, polycarbonate or mixtures thereof.

In embodiments of the invention, the body of the probe, the portion of the probe which is exposed to the interior of the bioreactor when the probe is in the operative position, and/or the first region of the probe are formed from medical grade plastics.

Additionally or alternatively, the body of the probe, the portion of the probe which is exposed to the interior of the bioreactor when the probe is in the operative position, and/or the first region of the probe may be formed of gamma sterilisable materials (i.e. which do not deform or soften upon exposure to gamma radiation at a dose of 10 kGy, about 20 kGy, about 25 kGy, about 30 kGy, about 35 kGy, about 40 kGy, about 50 kGy or about 80 kGy) and/or e-beam sterilisable materials (i.e. which do not deform or soften upon exposure to e-beam radiation of about 1 MeV, about 3 MeV, about 5 MeV or about 10 MeV).

Advantageously, it is not essential for application of the present invention that the biomass sensing probe is heat/steam sterilisable. Accordingly, in embodiments of the invention, the body of the probe, the portion of the probe which is exposed to the interior of the bioreactor when the probe is in the operative position, and/or the first region of the probe may be formed of materials which have a melting point of less than about 150 C.°, less than about 120° C., less than about 110° C., less than about 100° C. or less than about 80° C.

It has been recognised that the assembly of biomass sensing probes with adhesive may be problematic in certain applications as compounds within the adhesive can promote reactions within or otherwise contaminate or have other deleterious effects on biomass contained within the bioreactor. Additionally, adhesive used to produce the biomass sensing probe may, in use, become separated from the probe and travel into the biomass medium, which can exacerbate contamination or other adverse effects upon the medium. Accordingly, in certain embodiments of the invention, the body of the probe, the portion of the probe which is exposed to the interior of the bioreactor when the probe is in the operative position, and/or the first region of the probe may be free of adhesive.

In such embodiments, the body of the probe, the portion of the probe which is exposed to the interior of the bioreactor when the probe is in the operative position, and/or the first region of the probe may be formed by a moulding process.

In arrangements where the body of the probe, the portion of the probe which is exposed to the interior of the bioreactor when the probe is in the operative position, and/or the first region of the probe comprises separate probe body components requiring connection, this can be advantageously achieved without the use of adhesive through the selection of materials which are capable of being sealed together using solvents (e.g. methylene chloride, ethylene dichloride, acetone, or a mixture thereof), mechanical connection (e.g. snap fit, friction fit or the like), heat and/or ultrasound.

The inventors have found that the use of such adhesive-free sealing techniques can advantageously be used to form watertight seals of components used to produce biomass sensing probes. This is of particular importance in embodiments in which the interior of the biomass sensing probe comprises cavities and/or hollows as the leakage of biomass medium into the interior of the probe is undesirable, both from the perspective of contamination of the medium and also in terms of operation of the probe.

Thus, in embodiments of the invention, the biomass sensing probe comprises cavities and/or hollows in its interior and the portion of the probe which is exposed to the interior of the bioreactor when the probe is in the operative position, and/or the first region of the probe is watertight.

In this context, a determination of whether or not the probe is watertight can be made by submerging the portion of the probe which is exposed to the interior of the bioreactor when the probe is in the operative position, and/or the first region of the probe to water in a vessel at a temperature of 25° C. and a pressure of 1 bar for thirty minutes. Water ingress into the probe can be determined according to the following approaches:

Resistance testing: A measurement following submersion of the probe to determine resistance between the electrodes is taken. If a resistance of about 0.99 megaohm or less, about 0.98 megaohm, about 0.95 megaohm or about 0.9 megaohm is detected, this may be indicative of leakage.

Weight gain: The mass of the probe before and after submersion may be taken. A weight gain of less than about 0.1 g, less than about 0.05 g, less than about 0.02 g, less than about 0.01 g or 0 g indicates that no moisture has entered the probe.

In a further aspect, the invention provides a method of preparing a biomass sensing probe comprising an elongate body formed of a plurality of probe body components including at least one electrode provided on a first region of the body, the body of the probe comprising one or more cavities and or hollows in its interior, comprising: providing the plurality of probe body components; sealing the probe body components to produce the biomass sensing probe; wherein the seal formed between the probe body components in the first region of the body is watertight and adhesive-free.

In some embodiments of the invention, the seal formed between the probe body components in the entirety of the body is watertight and adhesive-free.

As explained above, adhesive-free seals between probe body components may be achieved through the use of solvents, mechanical connection, heat and/or ultrasound.

The probe of the present invention may be produced in a sterile and/or inert environment, e.g. in a clean room.

For the avoidance of doubt, the biomass sensing probe produced according to this aspect of the invention may have any of the properties or parameters discussed herein.

In embodiments of the invention, once assembled, the biomass probe may be calibrated. Those skilled in the art will be familiar with methods for calibrating biomass sensing probes.

In preferred embodiments of the present invention, the biomass sensing probe of the present invention is a single use probe. As those skilled in the art will recognise, single use biomass sensing probes, as their name suggests, are designed and intended to be used only once. The use of single use probes permits the use of less robust materials in the manufacture of the probes, primarily because the probes do not have to be resistant to repeated sterilisation procedures.

In embodiments of the invention, the bioreactor may be single use, or may be reusable.

Thus, according to a further aspect of the present invention, there is provided a method of obtaining a biomass measurement comprising: providing a system comprising a bioreactor having a wall enclosing an interior comprising a biomass, the wall comprising a port; a biomass sensing probe comprising an elongate body and at least one electrode provided on a first region of the body; the port being configured to receive the probe and form a watertight seal with the probe when the probe is located in an operative position within the port, wherein in the operative position the first portion of the body is exposed to the interior of the bioreactor; inserting the biomass sensing probe into the port in the operative position; obtaining the biomass measurement; and disposing of the probe.

In this aspect of the invention, the method may further comprise the steps of securing the biomass sensing probe in the operative position in the port, removing the probe from the port and/or disposing of the biomass sensing probe and/or the bioreactor once the biomass measurement has been taken.

According to a still further aspect of the present invention, the present invention provides a kit comprising a biomass sensing probe comprising an elongate body and at least one electrode provided on a first region of the body and instructions for using the biomass sensing probe with a bioreactor having a wall enclosing an interior, the wall comprising a port; the port being configured to receive the probe and form a watertight seal with the probe when the probe is located in an operative position within the port, wherein in the operative position the first portion of the body is exposed to the interior of the bioreactor and wherein the instructions specify that the biomass sensing probe should only be used once.

In this aspect of the invention, the kit may further comprise a bioreactor having a wall enclosing an interior, the wall comprising a port; the port being configured to receive the probe and form a watertight seal with the probe when the probe is located in an operative position within the port, wherein in the operative position the first portion of the body is exposed to the interior of the bioreactor.

The kit may additionally or alternatively comprise biomass signal processing means.

In embodiments of the invention, the probe and/or the bioreactor may be provided in the kit in sterile packaging.

The methods and systems of the present invention may be employed to take biomass measurements from any type of biological media. Biotechnological and brewing applications have been mentioned above, but these are merely illustrative. The biological medium (e.g. first, second and/or further biological media) may be liquid and contain a plurality of cells. The cells may be human, animal (mammal or other), bacterial, plant, stem, fungal (e.g. yeast) or other.

EXAMPLE

The present invention will now be described in the example which follows.

Example 1

FIG. 1 shows a probe body component, specifically a tip 1 bearing four electrodes 3, two of which are visible. Tip 1 is formed of polycarbonate, commercialised under the trade name Makrolon® Rx2530 commercialised by Bayer.

Figure 2:
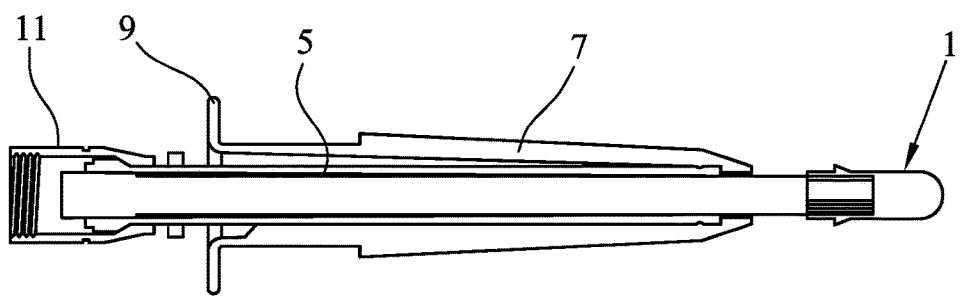
FIG. 2 is a side elevational view of the probe tip located in a biomass sensing probe. The shell (5) is broken away to show a core of the probe.

FIG. 2 shows how tip 1 is located in the biomass sensing probe. Tip 1 is positioned at the distal end of the probe. Other probe body components are shown, namely core 5 and shell 7. Core 5 is formed of polycarbonate, commercialised under the trade name Makrolon® Rx2530 and is hollow to provide a cavity via which conducting means (not shown) are located. Shell 7 is formed of polycarbonate, commercialised under the trade name Makrolon® Rx2530 and is provided with an annular flange 9 to prevent the over-insertion of the biomass sensing probe into the port. As can be seen, shell 7 has an outwardly tapering profile to facilitate the formation of a watertight seal with the port. The probe is also provided with coupling means in the form of a Redel push-pull connector 11.

Figure 3:
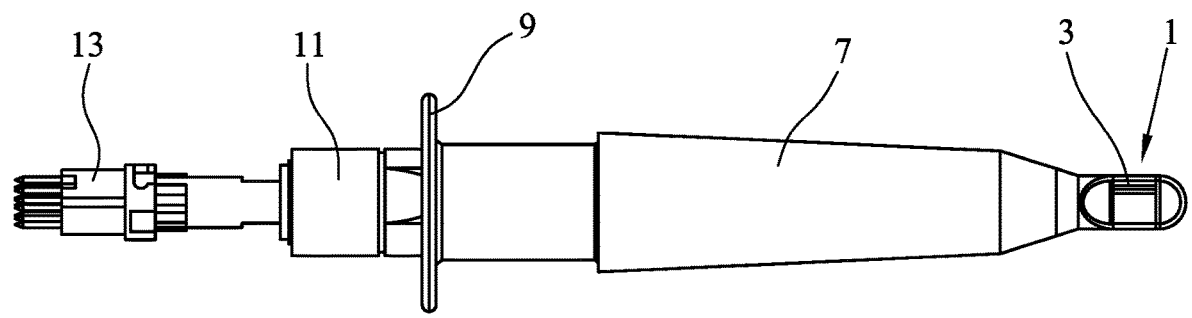
FIG. 3 is a side elevational view of an assembled biomass sensing probe.

FIG. 3 shows the assembled biomass sensing probe and illustrates how the electronic connector 13 is inserted to facilitate the transmission of biomass sensing signals from the electrodes 3 to the biomass signal processing means (not shown). The probe body components 3, 5 (not shown) and 7 are sealed together without the use of adhesive. Instead, the components are sealed by exposing the surfaces of the probe body components to be sealed to methylene chloride and securely held for one minute.

The seal strength was tested by submerging the distal end of the probe in water in a vessel that was pressurised to 2 bar for 30 minutes and checked for electrical resistance. The probe was also weighed before and after submersion. No drop in resistance nor weight gain of the probe was detected, indicating that no water had entered into the probe. In other words, the probe was found to be watertight.

FIG. 4 illustrates a port with which the probe shown in FIG. 3 can be used to form a watertight seal. The port comprises an annular flange 15 at the inner end of the port, an upstanding collar 19 which defines a channel 17 which runs through the port. The port is shown in cross section in FIG. 5 and as can be seen, the channel 17 is tapered, such that the channel is narrower at is inner end than at its outer end.

FIG. 6 shows the probe in the operative position in the port. As can be seen, the probe is fully inserted into the port such that the annular flange 9 of the probe abuts the outer end of the port. A portion of the probe body (specifically tip 1 and part of the shell 7) extend beyond the inner end of the channel 17. In use, the annular flange will be sealed to the wall of a bioreactor (not shown) and thus the portion of the probe body extending beyond the inner end of the channel will pass into the interior of the bioreactor, facilitating a biomass measurement being obtained. Bands 21 are applied to the collar 19 of the port to secure the probe in the operative position.

The invention claimed is:

1. A system for obtaining a biomass measurement from a medium contained within a bioreactor, the system comprising
   a bioreactor having a wall enclosing an interior, the wall comprising a port; and
   a biomass sensing probe comprising an elongate body comprising a core having a first end and a second end and a shell partially surrounding the core, the core and the shell formed of a plastic material, wherein the shell has a tapered profile and a flange, the elongate body further comprising a tip configured to be coupled to the first end of the core, and at least one electrode provided on a first region of the tip;
   the port comprising a channel having a longitudinal axis, wherein the profile of the channel is tapered, and the port is configured to receive the probe and form a watertight seal with the probe, the watertight seal being attained through the profile of the shell and the interior of the port when the probe is located in an operative position within the port, wherein the core extends beyond the shell at the first end such that, in the operative position, the first region of the tip is exposed to the interior of the bioreactor, wherein the flange is configured to prevent over-insertion of the probe into the port when the probe is received in the port, and wherein, in the operative position, the second end of the core extends beyond the shell.

2. The system of claim 1, wherein the longitudinal axis of the channel is perpendicular to the wall of the bioreactor.

3. The system of claim 1, wherein the channel is circular in cross-section.

4. The system of claim 1, wherein the biomass sensing probe comprises conducting means connected to the at least one electrode.

5. The system of claim 1, wherein the biomass sensing probe is modular.

6. The system of claim 5, wherein the body of the probe is free of adhesive.

7. The system of claim 5, wherein the core is hollow in its interior.

8. The system of claim 1, wherein the portion of the probe which is exposed to the interior of the bioreactor when the probe is in the operative position is formed of gamma sterilisable materials.

9. The system of claim 1, wherein the portion of the probe which is exposed to the interior of the bioreactor when the probe is in the operative position is formed of materials having a melting point of less than 100° C.

10. The system of claim 1, wherein the the port comprises over-insertion prevention means.

11. The system of claim 1, wherein the at least one electrode includes 2 to 6 electrodes.

12. The system of claim 1, wherein the core comprises a coupler configured to receive an electrical connector located at the second end of the core.

13. The system of claim 1, wherein the system further comprises biomass signal processing means.

14. The system of claim 1, wherein the biomass sensing probe and/or the bioreactor are configured for single use.

15. A method of obtaining a biomass measurement comprising:
   providing the system of claim 1;
   inserting the biomass sensing probe into the port in the operative position;
   obtaining the biomass measurement; and
   disposing of the probe.

16. The method of claim 15, further comprising securing the biomass sensing probe in the operative position in the port.

17. The method of claim 15, further comprising removing the probe from the port.

18. The method of claim 15, further comprising disposing of the bioreactor and/or the biomass sensing probe once the biomass measurement has been taken.

19. The system of claim 1, wherein the plastic material that forms the body of the biomass sensing probe is a polycarbonate.

20. The system of claim 12, wherein the coupler is located external to the port for receiving the electrical connector.

* * * * *